United States Patent [19]

Trauth

[11] Patent Number: 5,637,465
[45] Date of Patent: Jun. 10, 1997

[54] METHOD FOR THE DETECTION OF A PROGRAMMED OR INDUCED CELL DEATH OF EUKARYOTIC CELLS

[75] Inventor: Bernhard Trauth, Mannheim, Germany

[73] Assignee: Boehringer Mannheim GmbH, Mannheim, Germany

[21] Appl. No.: 245,583

[22] Filed: May 18, 1994

[30]     Foreign Application Priority Data

Jun. 3, 1993 [DE] Germany .......................... 43 18 402.2

[51] Int. Cl.⁶ .............................. G01N 33/53; C12Q 1/68
[52] U.S. Cl. ................... 435/7.1; 435/6; 435/7.2; 435/7.5
[58] Field of Search .................... 435/6, 7.2, 7.5, 435/975

[56]             References Cited

U.S. PATENT DOCUMENTS 4,496,654   1/1985   Katz et al. ........................... 435/7.9

OTHER PUBLICATIONS

Frankfurt et al, "Flow cytometry of apoptosis and the evaluation of chemosensitivity in chronic lymphocytic leukemia and lymphoma," Proc. of the Am. Ass. for Cancer Res., vol. 34, p. 288 Mar. 1993.

Thiry et al, "Ultrastructual distribution of histones within Ehrlich tumor cell nucleoli: A Cytochemical and immunocytochemical study", J. of Histochem. and cytochem., vol. 37, No. 6, pp. 853–862 1989.

Cohen, "Programmed Cell Death in the Immune System", Adv. Immunol. 50: 55–85 (1991).

Matzinger, "The JAM test: A simple assay for DNA fragmentation and cell death", J. Immunol. Meth. 145: 185–192 (1991).

Laurent–Crawford et al. "The Cytopathic Effect of HIV is Associated with Apoptosis" Virology, vol. 185(2), pp. 829–839, issued 1991.

Harlow et al, "Antibodies:A Laboratory Manual" pp. 321, 344, 555–556,583, 1988.

Naruse et al. "Antibody against single–stranded DNA detects both programmed cell death and drug–induced apoptosis" Histochemistry, vol. 101(1), pp. 73–78, issued Jan. 1994.

*Primary Examiner*—Toni R. Scheiner
*Assistant Examiner*—Yvonne Eyler
*Attorney, Agent, or Firm*—Felfe & Lynch

[57]              ABSTRACT

The invention concerns a method for the detection of a programmed or induced cell death of eukaryotic cells as well as a suitable test kit for this method of detection.

12 Claims, No Drawings

METHOD FOR THE DETECTION OF A PROGRAMMED OR INDUCED CELL DEATH OF EUKARYOTIC CELLS

The invention concerns a method for the detection of programmed or induced cell death of eukaryotic cells as well as a suitable test kit for this method of detection.

A eukaryotic cell can die in two fundamentally different ways. One way is necrosis, a death of the cell as a result of damage e.g. due to an insufficient supply of blood and thus an insufficient supply of oxygen and nutrients or as a result of poisoning or physical damage (mechanical injury, frost or heat). The other way, so-called programmed cell death, is of major importance for the development and functionality of tissues, organs and organisms as a whole (J. Cohen, Advances in Immunology 50 (1991), 55–85). Cells which have died in this manner exhibit DNA fragments associated with histones in the cytoplasm as mononucleosomes and oligonucleosomes. Such a manifestation is also observed in an induced cell death such as one which is produced for example by ionizing irradiation (Yamada et al., Int. J. Radiat. Biol. 53 (1988), 65) or by certain monoclonal antibodies such as e.g. anti-fas (Yonehara et al., J. Exp. Med. 169 (1989), 1747–1756) or anti-APO-1 (Trauth et al., Science 245 (1989), 301–304). Cytolytic T cells and natural killer cells also cause such an induced cell death with the described feature (Sanderson, Biol. Rev. 56 (1981), 153–197, S. Curnow et al., Cancer Immunol. Immunother. 36 (1993), 149–155 and Berke, Immunol. Today 12 (1991), 396–399).

However, they also cause an increased permeability of the plasma membrane such as is observed in necrosis (Krähenbühl et al., Immunol. Today 12 (1991), 399–402). The described type of programmed or induced cell death is denoted apoptosis (Wyllie et al., Int. Rev. of Cytol. 68 (1980), 251–301). It is characterized by vesicular protuberances of the plasma membrane, condensation of the cytoplasm and activation of an endogenous endonuclease. In contrast to necrosis, apoptosis is an active process of the eukaryotic cell. It is not caused by death of the cells through heating, freezing and thawing or by lysis with a lytically active antibody (R. Duke et al., Proc. Natl. Acad. Sci. 80 (1983), 6361–6365). The calcium- and magnesium-dependent endonuclease activated in apoptosis cleaves the DNA double strand into mononucleosomes and oligonucleosomes in the readily accessible linker regions between the nucleosomes. In contrast the DNA in the nucleosomes is closely associated with the core histones H2A, H2B, H3 and H4 and is therefore protected from cleavage by the endonuclease (Burgoyne et al., Biochem. J. 143 (1974), 67 and Stach et al., J. Neurochem. 33 (1979), 257). Therefore the "DNA ladder"—a pattern of DNA fragments with a length of ca. 180 base pairs or a multiple thereof (Wyllie, Nature 284 (1980), 555–556 and J. Cohen, Advances in Immunology 50 (1991), 55–85)—that is typical for apoptotic cells is detectable after extraction of the DNA and separation in an agarose gel. The plasma membrane of the cells remains intact in this early stage of apoptosis. Mononucleosomes and oligonucleosomes accumulate in the cytoplasm of the dying cell (Duke et al., Lymphokine Research 5 (1986), 289–299).

A number of test procedures have been developed for the detection of apoptosis. One of these is in particular the aforementioned detection of a "DNA ladder" in an agarose gel which serves as a qualitative standard method for the detection of apoptosis and for differentiating from necrosis. In other methods the cell population to be examined is usually pre-labelled with $^3$H- or $^{125}$I-labelled thymidine and after induction of the apoptosis and cell fractionation the portion of $^3$H or $^{125}$I label in the intact chromosomal DNA, the fragmented DNA and in the cell culture supernatant is determined by means of centrifugation steps (R. Duke et al., Proc. Natl. Acad. Sci. 80 (1983), 6361–6365 and R. Duke et al., Lymphokine Research 5 (1986), 289–299). A simplification of this method is the so-called JAM test in which the separation of intact DNA and DNA fragments is carried out by means of vacuum filtration through a glass fibre filter (P. Matzinger, J. Immunol. Meth. 145 (1991), 185–192). However, this method is very time-consuming and can only be carried out in special laboratories because of the use of a radioactive label. This is also true for another method for detecting apoptosis; described by P. Huang et al. in which the cellular DNA is purified, labelled with $^{32}$p at the 5' end after dephosphorylation and is separated electrophoretically in an agarose gel. The radioactivity is subsequently determined in the individual DNA bands (Annal. Biochem. 207 (1992), 163–167). A radioactive label is not required for the methods described by L. Meyaard Science 257: 217–259 (1992) et al. or W. Gorczyca et al., Intern J. Oncol. 1: 639–648 (1992) in which the DNA fragments produced by apoptosis are pre-labelled by means of nick translation with biotinylated dUTP and are then detected with fluorescence-labelled avidin. In another method the nuclear DNA is stained with an intercalating fluorescent dye such as acridine-orange after washing out the cytoplasmic, fragmented DNA and subsequently the fluorescence is measured. (F. Ojeda, J. Immunol. Meth. 152 (1992), 171–176). However, these methods are also very complicated for a routine cytotoxicity test to detect apoptosis and are limited to special laboratories due to the fluorescent dyes which are in some cases toxic and to the elaborate apparatus required.

The object of the invention was therefore to provide a simple cytotoxicity test which can be rapidly carried out for the detection of apoptosis.

This object is achieved by a method for the detection of programmed or induced cell death which is characterized in that a) a lysate of the cell population to be examined obtained by treatment with a non-ionic detergent is incubated with an anti-histone antibody and an anti-DNA antibody, wherein one of the two antibodies is bound to a solid phase before or after this incubation and the other antibody is a labelled antibody, b) the solid and liquid phase are separated and c) the label is determined in one of the two phases as a measure of the programmed or induced cell death.

It has surprisingly turned out that cells which have died by programmed or induced cell death (apoptotic cells) yield a measurable signal using this simple method without the need for pre-labelling of the cell population to be examined. As a result it is also possible to examine non-proliferating cells in vitro. The method according to the invention enables a simple quantitative determination in a very rapid manner of the extent of apoptosis in the cell population to be examined and is very sensitive so that only small amounts of cells (50 cells per test already yield a signal, $10^3$ cells per test are preferably used) are necessary to carry out the test.

In order to release cytoplasmic DNA fragments from apoptotic cells, the cell population to be examined is treated with a non-ionic detergent. Such detergents are known to a person skilled in the art. NP-40 (ethylphenyl polyethyleneglycol), Tween 20 (polyoxyethylenesorbitan monolaurate) or Triton X-100 (octylphenol polyethylene glycol ether) are preferred. These detergents are used at a concentration of 0.1% to 1%. The incubation of the apoptotic cells with the detergent preferably is carried out at room temperature or 4° C. for 10 to 30 minutes. The lysate obtained in this way is incubated with an anti-histone antibody as well as with an anti-DNA antibody after separation of the insoluble components (cell nuclei, e.g. by centrifugation). In this process either the anti-histone antibody or the anti-DNA antibody is bound to a solid phase. This binding is achieved either before or after incubation of the antibody with the cytoplasmic cell lysate in a manner known to a person skilled in the art e.g. by means of a direct adsorptive binding to a solid phase, by binding of a biotinylated antibody to a solid phase coated with streptavidin or binding to an antibody immobilized in an appropriate manner which is directed towards the anti-histone antibody or the anti-DNA antibody. Any antibody which reacts with one of the nucleosomal histones H2A, H2B, H3 and/or H4 can be used as the anti-histone antibody. Any antibody which binds to DNA can be used as the anti-DNA antibody. Such antibodies are described for example in Andre-Schwartz et al., Clin. Immunol. Immunopathol. 31 (1984), 261 or Eilat, Immunol. Today 6 (1985), 123. The anti-histone antibody as well as the anti-DNA antibody can be used as a complete immunoglobulin or as a binding fragment of an immunoglobulin such as an Fab or $F(ab')_2$.

The second antibody, i.e., the one which is not immobilized to the solid phase is used for labelling. For this purpose this antibody can either be itself labelled or become labelled by addition of a further labelled antibody which is directed towards the anti-DNA antibody or the anti-histone antibody. Labelling in this case is carried out according to methods well-known to a person skilled in the art e.g. by means of enzymes, fluorescent or chemiluminescent dyes. The label associated with the solid phase after separation of the solid from the liquid phase is a direct measure of the extent of apoptosis in the examined cell population. In each case a parallel culture of the examined cell population in which no apoptosis has been induced is used as the negative control. The label associated with the solid phase measured with this parallel culture yields the blank value for the determination. Those measured values for the label associated with the solid phase that are at least two-fold above this blank value are rated as being positive for apoptosis. If it is intended to determine apoptosis induced in vitro, the cell population to be examined is divided into two parallel preparations and then incubated in the presence or absence of the apoptosis-inducing agent (e.g. camptothecin).

In a preferred embodiment of the method according to the invention the antibody used for the immobilization is biotinylated in order to bind it to the solid phase and a solid phase coated with streptavidin is used.

With the aid of the method according to the invention it is possible to determine in a simple manner the cytotoxicity of cells or compounds which induce apoptosis.

The invention also concerns the use of the method to determine the cytotoxic effect or activity of cytolytic cells, natural killer cells, ionizing radiation or chemical substances such as monoclonal antibodies, hormones (e.g. glucocorticoids) or toxins (e.g. dioxins). The cytotoxic effect or activity is determined by the extent of apoptosis found in accordance with the invention.

The invention also concerns a reagent kit for the detection of programmed cell death which comprises an anti-histone antibody as well as an anti-DNA antibody. In this case one of the two antibodies is preferably present in a labelled form. Alternatively the kit can, however, also contain a further labelled antibody which is directed either towards the anti-histone antibody or towards the anti-DNA antibody.

A preferred embodiment of the invention is finally a reagent kit according to the invention in which one of the two antibodies is present in a biotinylated form for binding to a solid phase and which in addition contains a solid phase coated with avidin or streptavidin.

The invention is elucidated further by the following example.

EXAMPLE 1

Detection of Apoptotic Cells

1. Induction of Apoptosis

Cells of the human promyeloid leukemic cell line HL60 (ATCC CCL 240) in the exponential growth phase are adjusted to a cell concentration of $10^5$ cells per ml with culture medium and 500 µl of this is incubated in each case for 4 hours at 37° C. and 5% $CO_2$ with 500 µl of a solution of the topoisomerase I inhibitor camptothecin (0–4 µg camptothecin/ml in culture medium, in which case the value 0 µg/ml serves as a negative control).

2. Sample Preparation

After incubation, the cells are centrifuged at 200 g for 5 min, the supernatant is aspirated and the cell pellet is resuspended in 1 ml culture medium. After centrifuging again under the same conditions, the cell pellet is resuspended in 500 µl incubation buffer (see below), mixed well and incubated for about 30 minutes at 4° C. The lysate obtained in this way is centrifuged for 10 minutes at 20,000 g and 400 µl of the supernatant (cytoplasmic fraction) is carefully removed without stirring up the pellet (cell nuclei with high molecular, non-fragmented DNA). The supernatant obtained in this way is prediluted 1:10 with incubation buffer for the subsequent immunoassay.

Incubation Buffer:

PBS pH 7.4 with 0.2% Tween 20, 1% bovine serum albumin and 5 mmol/l EDTA, in which PBS=137 mmol/l NaCl 2.7 mmol/l KCl, 8 mmol/l $Na_2HPO_4$ and 1.5 mmol/l $KH_2PO_4$.

3. Immunoassay

In order to bind the anti-histone antibody to a microtitre plate, 100 µl coating solution ($Na_2HCO_3$/$NaH_2CO_3$ 50 mmol/l pH 9.6) is pipetted into each well of a microtitre plate and incubated for 1 hour at room temperature. Subsequently the coating solution is carefully aspirated and 200 µl incubation buffer are pipetted into each well of the microtitre plate for the recoating, incubated for 30 minutes at room temperature and the liquid is carefully removed by aspiration. Subsequently the wells are rinsed 3x with 250–300 µl washing solution (PBS (see section 2)+0.1% Tween 20) each time. After addition of 100 µl sample solution (see section 2) per well of the microtitre plate, it is incubated for 90 minutes at room temperature and then washed three times as described above. In order to detect bound apoptotic DNA fragments from the sample solution, 100 µl of a peroxidase-labelled anti-DNA antibody is then added, incubated for 90 minutes at room temperature and again washed three times as described above. Subsequently 100 µl ABTS® substrate solution for the peroxidase reaction is added and it is mixed on a plate shaker until the colour development enables a photometric evaluation at 405 nm against the substrate solution as the blank value (10–20 min). The ratio of the measured absorbance of the sample solution to the measured absorbance of the control mentioned in section 1 (living cells without induction of apoptosis) yields a concentration factor which is a measure of the portion of apoptotic cells in the examined cell population.

I claim:

1. Method for determining programmed or induced cell death in a cell sample, comprising:
   (i) treating a portion of said cell sample with a non-ionic detergent which lyses the cell membrane of cells in said cell sample but not the nuclear membrane of said cells, to obtain a cytoplasmic cell lysate;
   (ii) incubating said cytoplasmic cell lysate under conditions favoring binding of a first antibody to a histone, and a second antibody to DNA, to form a complex between said first antibody, said histone, said DNA, and said second antibody;
   (iii) binding said complex to a solid phase;
   (iv) separating said solid phase from said cytoplasmic cell lysate,; and
   (v) determining said complex as a determination of programmed or induced cell death.

2. The method of claim 1, wherein one of said first antibody and said second antibody is biotinylated, and said solid phase comprises avidin or streptavidin.

3. The method of claim 1, wherein one of said first antibody and said second antibody is labelled.

4. The method of claim 1, further comprising determining said complex by contacting complex bound to solid phase with a third antibody which binds to the first or second antibody not bound to solid phase.

5. Method for determining programmed or induced cell death in a cell sample, comprising:
   (i) treating a portion of said cell sample with a non-ionic detergent which lyses the cell membrane of cells in said cell sample but not the nuclear membrane of said cells, to obtain a cytoplasmic cell lysate;
   (ii) incubating said cytoplasmic cell lysate under conditions favoring binding of a first antibody to a histone, and a second antibody to DNA, wherein one of said first antibody and second antibody is labelled, to form a labelled complex of first antibody, histone, DNA, and said second antibody;
   (iii) binding said complex to a solid phase via the first or second antibody which is not labelled;
   (iv) separating said solid phase from said cytoplasmic cell lysate; and
   (v) determining labelled antibody on said solid phase or in said cytoplasmic cell lysate as a determination of programmed or induced cell death.

6. The method of claim 5, wherein the first or second antibody which is not labelled is biotinylated, and said solid phase comprises avidin or streptavidin.

7. The method of claim 1, wherein one of said first and second antibodies is bound to a solid phase when contacted to said lysate.

8. The method of claim 5, wherein the one of said first and second antibodies not labelled is bound to a solid phase when introduced to said lysate.

9. Method for determining cytotoxic effect of an agent on a cell type, comprising introducing said agent to a sample of said cell type, lysing said sample of said cells type with a non-ionic detergent which lysis the cell membrane of cells in said cell sample but not the nuclear membrane of said cells in said cell sample, to obtain a cytoplasmic cell lysate, contacting said lysate with a first antibody which specifically binds to histone and a second antibody which specifically binds to DNA, and determining formation of complexes containing both said first and said second antibody as a determination of cytotoxic effect of said agent.

10. The method of claim 1 or 5, wherein said portion of cell sample contains about $10^3$ cells.

11. The method of claim 1, wherein said portion of cell sample contains about 50 cells.

12. The method of claim 1 or 5, wherein said histone is H2A, H2B, H3, or H4.

* * * * *